United States Patent [19]
Podszun et al.

[11] Patent Number: 6,001,535
[45] Date of Patent: Dec. 14, 1999

[54] MONOMERS WITH CYCLIC CARBONATE GROUPS

[75] Inventors: Wolfgang Podszun, Köln; Ludger Heiliger, Leverkusen; Michael Müller, Bergisch Galdbach; Carl Casser, Köln; Friedrich Bruder, Krefeld, all of Germany

[73] Assignee: Agfa Gevaert AG, Germany

[21] Appl. No.: 08/999,983

[22] Filed: Oct. 1, 1997

Related U.S. Application Data

[63] Continuation of application No. 08/581,606, filed as application No. PCT/EP94/02666, Feb. 11, 1994, abandoned.

[30] Foreign Application Priority Data

Jul. 22, 1993 [DE] Germany .......................... 43 24 614.1

[51] Int. Cl.$^6$ .............................. G03F 7/028; G03F 7/32; G03F 7/34
[52] U.S. Cl. ...................... 430/285.1; 430/302; 430/258; 430/260; 430/281.1; 522/169; 549/448; 549/454; 549/229
[58] Field of Search ................................ 430/285.1, 302, 430/258, 260, 281.1; 522/169; 549/748, 454, 229

[56] References Cited

U.S. PATENT DOCUMENTS

| | | | |
|---|---|---|---|
| 3,619,260 | 11/1971 | Parker | 526/314 |
| 5,047,261 | 9/1991 | Moussa et al. | 522/169 X |
| 5,374,699 | 12/1994 | Iwamura et al. | 526/314 |

FOREIGN PATENT DOCUMENTS

| | | | |
|---|---|---|---|
| 3-635A | 1/1991 | Japan | 526/314 |
| 2-270106 | 5/1992 | Japan | 526/314 |
| 4-258659 | 9/1992 | Japan | 526/314 |

OTHER PUBLICATIONS

CA 112:217573 of Brosse et al, Makromol. Chem. Rapid Commun. (1990), 11(3), 123–8.
CA 113:98071 of Decker et al, Makromol. Chem. Rapid Commun. (1990), 11(4), 159–67.
CA 121:85776 of Decker et al, Rad Tech Asia '91 Conference Proc. (1991), 335–9.
Chemical Abstracts, vol. 112, No. 24, published 1990, Jun. 11, (Columbus, Ohio, USA), J.C. Brosse et al. "Acrylic monomers containing a cyclic carbonate function. 1. Synthesis and polymerization", p. 2, No. 217 573e.
Chemical Abstracts, vol. 113, No. 12, published 1990, Sep. 17, (Columbus, Ohio, USA), C. Decker et al. "A new class of highly reactive acryulic monomers. 1. Ligh–induced polymerization," p. 3, No. 98 071y.
Chemical Abstracts; vol. 114, No. 14, published 1991, Apr. 8, (Columbus, Ohio, USA), D. Couvret et al. "New functionalization method for radiation curable polyurethanes containing pendant acrylate groups", p. 109, No. 124 568h; & Eur. Plyzm. J. 1991, 27 (2), 193–7.
Chemical Abstracts, vol. 114, No. 22, published 1991, Jun. 3, (Columbus, Ohio, USA), C. Decker et al. "A new class of highly reactive acrylic monomers. 2. Light–induced copolymerization with difunctional oligomers", p. 5, No. 207 909w.
J.C. Brosse et al. "Acrylic monomers containing a cyclic carbonate function. 1. Synthesis and polymerization", Makromol. Chem., Rapid Commun. 1990, 11(3), pp. 123–128.
C. Decker et al. "A new clas of highly reactive acrylic monomers. 1. Light–induced polymerization," Makromol. Chem., Rapid Commun. 1990, 11(4), pp. 159–167.
Decker et al. "A new class of highly reactive monomers. 2. Light–induced copolymerization with difunctional oligomers", Mackromol. Chem. 1991, 192(3), pp. 507–522.
Covret et al, "New Functionalization Method for Radiation Curable Polyurethanes Containing Pendant Acrylate Groups", European Polymer Journal, vol. 27, No. 2, pp. 193–197, 1991.

Primary Examiner—Cynthia Hamilton
Attorney, Agent, or Firm—Connolly Bove Lodge & Hutz LLP

[57] ABSTRACT

Monomers with cyclic carbonate groups of the formula I are suitable for the production of photosensitive recording materials, for example for the production of offset printing plates

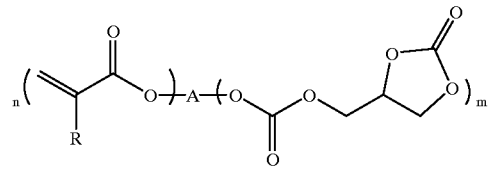

in which A means an (n+m)-valent hydrocarbon residue with 3 to 30 C atoms, which may be OH-substituted and may contain up to 8 ether bridges, R means H or methyl;

n means an integer from 1 to 5;

m means an integer from 1 to 3, providing that n+m is at least 3.

5 Claims, No Drawings

MONOMERS WITH CYCLIC CARBONATE GROUPS

This application is a continuation of Ser. No. 08/581,606 which was filed Jan. 11, 1996 and is now abandoned, which in turn is a 371 of PCT/EP94/102266 filed Jul. 11, 1994.

The present invention relates to acrylates and methacrylates with cyclic carbonate groups, and to photosensitive recording materials containing these (meth)acrylates.

Recording materials based on methacrylates and acrylates are well known. In these recording materials, photopolymerisation is initiated by imagewise exposure with actinic radiation. The copying methods are based on the principle of differentiating the properties of the exposed and unexposed parts of the photopolymerisable layer, for example differentiation in terms of solubility, adhesion, conductivity, refractive index, tackiness, permeability or diffusibility of penetrating substances, such as for example dyes.

Copying systems based on a difference in tackiness are described in U.S. Pat. Nos. 3,060,024, 3,085,488 and 3,649,268. According to the method disclosed in these U.S. Pat. the photopolymerisable layer loses its tackiness in the areas exposed with the image, while the unexposed areas remain tacky. The unexposed areas may thus be coloured with dry pigments in order to render the image visible.

Further copying methods based on photopolymerisation with subsequent dry development are described in U.S. Pat. No. 3,245,796, EP-A-0 362 827, U.S. Pat. No. 4,587,198 and U.S. Pat. No. 3,060,023.

As explained above, photopolymerisation is used in many ways for image reproduction. Methods using both wet and dry image development have been used for this purpose. The latter methods are particularly easy to use and have considerable ecological advantages. However, the optical resolution which may be achieved with dry developable photopolymerisable compositions is relatively low. This low resolution constitutes a particular problem when reproducing finely patterned images. Furthermore, the energy sensitivity of known dry developable materials is relatively low.

EP-A 0 406 057 proposes monofunctional (meth)acrylates with cyclic carbonate groups for coatings.

The object of the present invention is to provide (meth)acrylates which have elevated photopolymerisability and may be used for dry processable recording materials. Further objects of the present invention will become apparent from the following specification.

The present invention provides (meth)acrylates with cyclic carbonate groups according to the following formula I

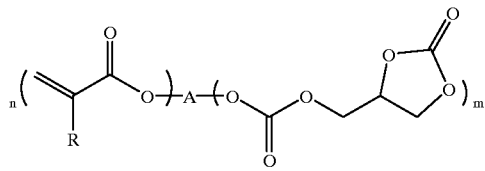

in which

A means an (n+m)-valent hydrocarbon residue with 3 to 30 C atoms, which may be OH-substituted and may contain up to 8 ether bridges, R means H or methyl;

n means an integer from 1 to 5;

m means an integer from 1 to 3, providing that n+m is at least 3.

The hydrocarbon residue is preferably an aliphatic hydrocarbon residue, which may be linear, branched or cyclic. Linear or branched residues are particularly preferred. The following are examples of particularly suitable hydrocarbon residues A:

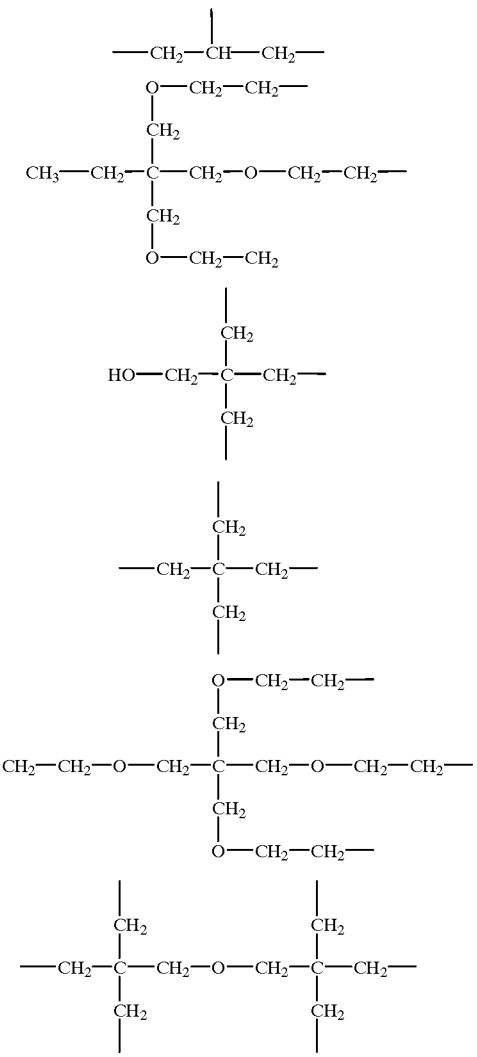

(Meth)acrylates according to the invention are shown in the following table 1.

TABLE 1
Monomer 1
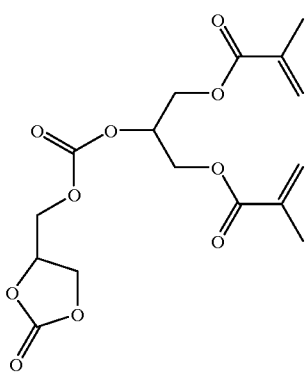
Monomer 2
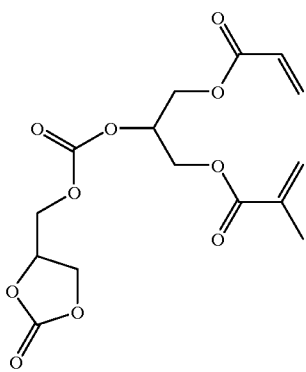
Monomer 3
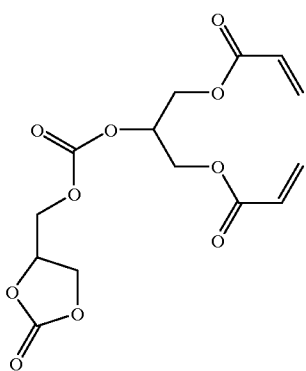
Monomer 4
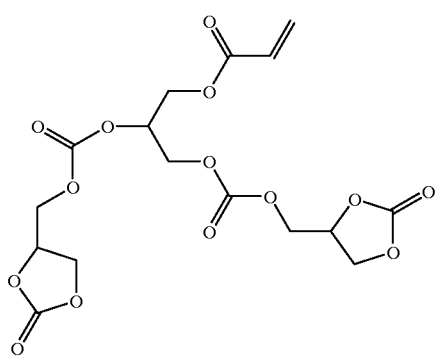
TABLE 1-continued
Monomer 5
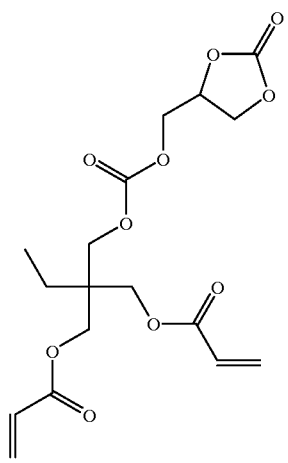
Monomer 6
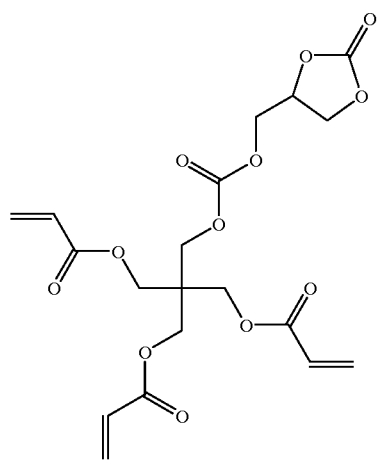
Monomer 7
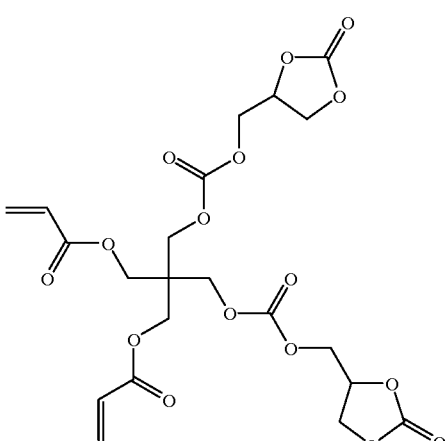

TABLE 1-continued

Monomer 8

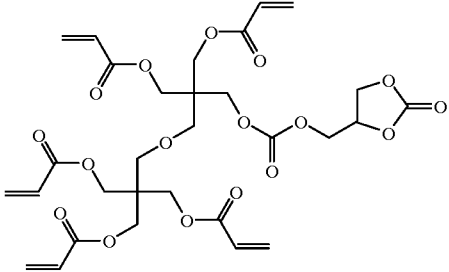

Monomer 9

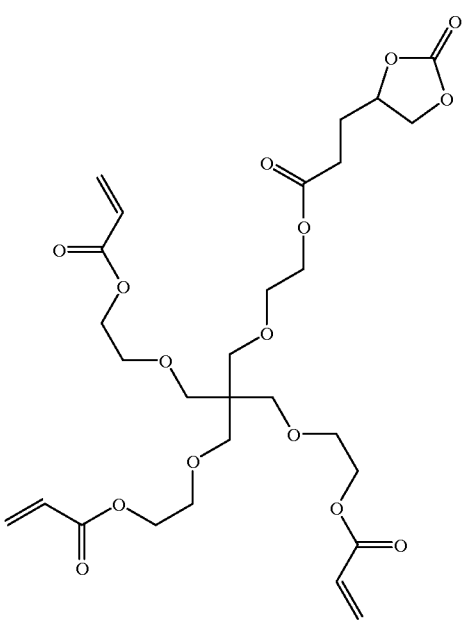

The (meth)acrylates with cyclic carbonate groups according to the invention are conveniently synthesised by reacting the underlying hydroxyalkyl (meth)acrylate with the chloroformic acid ester according to the formula II Formula II:

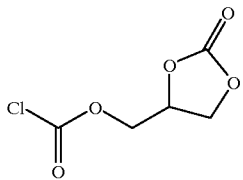

The chloroformic acid ester according to the formula II may be produced by phosgenating glycerol. This stage of the synthesis is exhaustively described in U.S. Pat. No. 2,446,145.

(Meth)acrylates according to the invention may also be obtained by reacting polyhydroxy compounds with a functionality of at least 3 with mixtures prepared from (meth) acrylic acid chloride and the chloroformic acid ester of the formula II, wherein at least 1 mol of (meth)acrylic acid chloride and at least 1 mol of chloroformic acid ester of the formula II are used per mol of polyhydroxyl compound. The components are preferably used in a stoichiometric ratio. Mixtures of (meth)acrylates are generally produced in this reaction. It has been found that such mixtures exhibit good properties and may be used in the recording materials according to the invention without separation.

The present invention also provides a photosensitive recording material with at least one photosensitive layer arranged on a support, which layer contains monomers of the formula I and at least one photoinitiator.

In addition to the monomers of the formula I, the recording material may contain further monomers not falling within the formula I. The following may be cited by way of example: ethylene glycol diacrylate, diethylene glycol diacrylate, triethylene glycol diacrylate, tetraethylene glycol diacrylate, 1,4-butane diacrylate, hexamethylene diacrylate, cyclohexane dimethacrylate, glycerol diacrylate, glycerol triacrylate, trimethylolpropane triacrylate, pentaerythritol triacrylate, pentaerythritol tetraacrylate, dipentaerythritol pentaacrylate and dipentaerythritol hexaacrylate, together with the corresponding methacrylates. Further suitable monomers are so-called epoxy acrylates, such as, for example, bisphenol A diglycidyl dimethacrylates and urethane acrylates, which may be obtained by reacting (poly) isocyanates with hydroxyalkyl (meth)acrylates. Urethane acrylates according to EP-A-0 502 562 and European Patent Application no. 92 202 631, filed on 31.08.92, are particularly suitable.

The proportion of monomers according to the formula I should be 5–100%, preferably 10–100%.

The photoinitiators used are preferably those polymerisation initiators which are thermally inactive at temperatures of below 185° C. and may be activated with actinic light. Examples of such initiators include substituted and unsubstituted polycyclic quinones, i.e. compounds with two carbonyl groups attached to ring carbon atoms in a conjugated, six-membered carbocyclic ring, wherein at least one aromatic carbocyclic ring is fused to the ring bearing the carbonyl groups. Such initiators include: 9,10-anthraquinone, 1-chloroanthraquinone, 2-chloroanthraquinone, 2-methylanthraquinone, 2-tert.-butylanthraquinone, octamethylanthraquinone, 1,4-naphthoquinone, 9,10-phenanthrenequinone, 1,2-benzanthraquinone, 2,3-dichloronaphthoquinone, anthraquinone c-sulphonic acid sodium salt, 3-chloro-2-methylanthraquinone and 1,2,3,4-tetrahydrobenzo [a]-anthracene-7,12-dione. Further usable photoinitiators are described in U.S. Pat. No. 2,760,863 and include vicinal ketaldonyl compounds such as diacetyl, benzil, α-ketaldonyl alcohols such as benzoin, pivalon, acyloin ethers, such as for example benzoin methyl and ethyl ether; α-hydrocarbon substituted aromatic acyloins including methylbenzoin, α-allylbenzoin and α-phenylbenzoin. Further suitable photoinitiators are described in Photoreactive Polymers by Arnost Reiser, *Organic photochemical imaging systems* by G.A. Delzenne, in *UV*-Curing *Chemistry: Past, Present and Future* by Christian Decker, published in *Journal of Coatings Technology*, vol. 59, No. 751, Aug. 1987, pages 97–106 and in EP-A-0 362 827 and U.S. Pat No. -A-3,558,309.

According to the present invention, polymerisation inhibitors may also be added to the photopolymerisable composition. Suitable inhibitors are, for example, p-methoxyphenol, hydroquinone, alkyl- and acyl-substituted hydroquinones and quinones, tert.-butylpyrocatechol, pyrogallol, copper compounds, naphthylamines, β-naphthol, copper(II) chloride, 2,6-bis-tert.-butyl-p-cresol, photothiazine, pyridine, nitrobenzene and dinitrobenzene, p-toluquinone and chloranil.

The recording material of the present invention may contain further layers, for example a layer to improve the adhesion of the photopolymerisable layer onto the support or a stripping layer. It may be advantageous to arrange a functional layer between the support and the photosensitive photopolymerisable layer immediately adjoining the latter layer, which functional layer contains, for example, a polymer with polymerisable, ethylenically unsaturated groups. Such a functional interlayer is described, for example, in European Patent Application 91 201 824.9 (12.07.91).

The recording material according to the invention is produced by casting from solvents, in particular organic solvents. Examples of suitable solvents are chloroform, dichloromethane, acetone, methyl ethyl ketone, ethyl acetate, THF, methyl tert.-butyl ether. Methyl ethyl ketone is preferred.

The recording material according to the invention is exposed to actinic radiation distributed in accordance with the image in order entirely or partially to cure it in accordance with the distribution of the actinic radiation defined by the image. Exposure may be a contact exposure with ultraviolet radiation, exposure by means of a camera, a scanning exposure or exposure with a laser. Daylight, incandescent lamps, mercury vapour lamps, halogen lamps, xenon lamps, fluorescent lamps, light emitting diodes or lasers may be used as the light source. Care must of course be taken to ensure that the emission spectrum of the light source and the absorption spectrum of the photoinitiator have a usable overlap region.

The polymer image obtained by exposure may be converted into the desired final image for the particular application. It may, in particular, be used to produce black-&-white images, colour images and printing plates.

For example, in order to produce colour images, at least three recording elements containing a yellow dye, a magenta dye and a cyan dye or corresponding coloured pigments in or beneath the polymerisable composition are, for example, exposed imagewise with a scanned blue, green or red colour separation of the original. A fourth imaging element containing a black dye or pigment may optionally also be used. These imaging elements are consecutively brought into contact with an acceptor element, for example paper, under the action of heat to effect the transfer of the individual colour separations. Obviously, the various colour separations must be transferred in correct registration in order to obtain faithful colour reproduction of the original image.

In a particular embodiment of the present invention, the recording material is used for the production of printing plates. In this application, the polymer image produced by exposure may be produced directly on the printing plate substrate or may be transferred onto the printing plate substrates by a donor element.

Supports with hydrophilic surfaces, for example metal supports such as aluminium or zinc, polyester film or paper substrates may be used as printing plate substrates.

These supports may, if they are not themselves sufficiently hydrophilic, first be coated with a hydrophilic layer. A particularly suitable hydrophilic layer is a layer of polyvinyl alcohol cured with a tetraorthosilicate, for example a tetramethyl orthosilicate or tetraethyl orthosilicate containing $TiO_2$, as described, for example in U.S. Pat. No. 3,971,660.

Aluminium is a particularly suitable metal support. Suitable aluminium supports for use according to the present invention are aluminium foils made from pure aluminium or an aluminium alloy with an aluminium content of least 95%. A suitable alloy contains, for example, 99.55 wt% of aluminium, 0.29 wt.% of iron, 0.10 wt.% of silicon, 0.004 wt. % of copper, 0.002 wt.% of manganese, 0.02 wt. % of titanium and 0.03 wt. % of zinc. The thickness of such a foil is conventionally between 0.13 and 0.5 mm.

Production of an aluminium or aluminium alloy foil suitable for lithographic offset printing comprises the following stages: roughening, anodising and, optionally, sealing.

Roughening and anodising of the film are necessary in order to make it possible to produce high quality printed output according to the present invention. Sealing is not necessary, but may further increase print quality.

The aluminium surface may be roughened mechanically or electrolytically in a known manner. The roughness achieved by roughening is measured as the deviation in $\mu$m from a median line and is preferably approximately 0.2 to 1.5 $\mu$m.

The aluminium foil may be anodised in electrolytic baths, for example chromic acid, oxalic acid, sodium carbonate, sodium hydroxide and mixtures thereof. Anodisation of the aluminium and dilute aqueous sulphuric acid is preferably performed until the desired thickness of the anodised layer is achieved. The aluminium foil may be anodised on both sides. The thickness of the anodised layer is exactly determined from a microsection, but may also be determined by dissolving the anodised layer and weighing the foil before and after the dissolving treatment. Good results are achieved with an anodised layer of approximately 0.4 to approximately 2.0 $\mu$m. In order to improve image sharpness and consequently the sharpness of the printed copy, the anodised layer may be through-coloured with an anti-halo dye or pigment, as for example described in JP-A-58-14797.

After anodisation, the anodic surface may be sealed. Sealing the pores of the aluminium oxide layer formed during anodisation is a known technique, which is, for example, described in Belgisch-Nederlands tijdschrift voor oppervlaktetechnieken van materialen, vol. 24, Jan. 1980. Various methods for sealing porous, anodised aluminium surfaces are known. An advantageous method is hydration sealing in which the pores are entirely or partially closed by water absorption, such that hydrated acicular crystals of aluminium oxide (boehmite) are formed. To this end, the anodised surface of the aluminium foil may be treated with water at 70 to 100° C. or with steam. The water may contain additives for this purpose, for example nickel salts, in order to improve the sealing effect. Sealing may also be achieved by treating the anodic surface with an aqueous solution of phosphate ions or silicates. Sealing treatment renders the anodic layer substantially non-porous, such that it is suitable for the production of a larger number of printed copies. As a result of the sealing treatment, the occurrence of fogging in the non-image areas of the printing plate may largely be avoided.

Roughening, anodisation and sealing of the aluminium foil may be performed as, for example, described in U.S. Pat. No. 3,861,917.

The recording material according to the invention may be developed in the conventional manner, i.e. by wet development in order to produce a printing plate. In this method, development is performed using a solvent which dissolves the non-polymerised portions of the recording material while not dissolving the polymerised portions of the exposed recording material. organic solvents, in particular alcohols, are suitable solvents. Mixtures of water and alcohol are also suitable.

The recording material according to the invention may be processed to produce a printing plate using dry methods by transfer and delamination processes. According to a particular embodiment of the dry process, a donor element substantially consisting of a photosensitive layer which contains the monomers according to the invention and a support material, for example a polyethylene terephthalate film, is exposed with the image and brought into contact at elevated temperature with a hydrophilic printing plate substrate using a roller laminator; this transfers the non-polymerised portions imagewise from the donor element onto the acceptor element. The donor and acceptor element are then separated from each other, so producing a monomer image on the printing plate substrate. This monomer image is suitable as a printing form. Particularly stable printing forms are obtained if the monomer image is converted into a polymer image by uniform exposure or heating.

The recording materials according to the invention exhibit a particularly high energy sensitivity and produce images with elevated resolution and acutance. They may advantageously be used for dry imaging systems.

EXAMPLES

Example 1
Production of Monomer 1 from Table 1

18.25 g of glycerol dimethacrylate (Blemmer GMR from Nippon Oil) and 4.56 g of pyridine were dissolved in 32.5 ml of methylene chloride and the solution was cooled to 0° C. 9.93 g of chloroformic acid ester of the formula II, dissolved in 17.5 g of methylene chloride, were then slowly apportioned and the mixture was stirred for a further 2 hours at room temperature. The resultant precipitate was filtered out and the filtrate poured into twice its volume of water. The organic phase was separated, extracted twice with 0.1 n hydrochloric acid, then with sodium hydrogen carbonate solution and finally washed with water and dried over sodium sulphate. Once the mixture had been filtered and the solvent evaporated, there remained 20.9 g of monomer 1 from table 1.

IR [cm$^{-1}$]: 1820 (cyclic carbonate); 1760 (carbonate); 1725 (ester); 1645 (methacrylic)

Example 2

Production of monomer 2 from table 1

The test was performed as described in example 1, wherein glycerol acrylate-methacrylate (Blemmer GAM from Nippon Oil) was used instead of glycerol dimethacrylate.

IR [cm$^{-1}$]: 1820 (cyclic carbonate); 1760 (carbonate); 1725 (ester); 1640, 1620 (methacrylic, acrylic)

Example 3
Production of Monomer 6 from Table 1

The test was performed as described in example 1, wherein pentaerythritol triacrylate was used instead of glycerol dimethacrylate.

IR [cm$^{-1}$]: 1815 (cyclic carbonate); 1760–1720 (ester and carbonate); 1635–1620 (acrylic)

Example 4
Production of Monomer 8 from Table 1

The test was performed as described in example 1, wherein dipentaerythritol dimethacrylate was used instead of glycerol dimethacrylate.

IR [cm$^{-1}$]: 1815 (cyclic carbonate); 1760–1720 (ester and arbonate); 1635–1620 (acrylic)

Example 5
Testing of Photoreactivity of the Monomers using Photo-DSC

The following constituents were vigorously mixed:
50.0 g of monomer
120 mg of 2,6-di-tert.-butylcresol
200 mg of camphorquinone
500 mg of p-dimethylaminobenzenesulphonic acid N,N-diallylamide 2,6-Di-tert.-butylcresol acts as a stabiliser; camphorquinone and p-dimethylaminobenzenesulphonic acid N,N-diallylamide form the photoinitiator system.

The samples were irradiated at 30° C. in a DSC (differential scanning calorimetry) apparatus with a halogen lamp (75 W) with a heat protection filter. Heat flow was recorded as a function of time while the sample was irradiated. Samples of the same composition without the photoinitiator were used as the reference. The t-max value was determined as a measure of reaction rate. t-max is the time from the beginning of irradiation until the reaction maximum is reached (maximum heat flow).

The lower is the value for t-max, the greater is the photoreactivity.

| Monomer | t-max [min] |
| --- | --- |
| from example 1 | 0.50 |
| from example 2 | 0.44 |
| from example 3 | 0.31 |
| from example 4 | 0.48 |
| trimethylolpropane trimethacrylate (comparison) | 2.0 |

Example 7
Production of an Offset Printing Plate by Wet Development
a) Production of a hydrophilic printing plate substrate The following substances were added in succession to 418 g of a dispersion of 21.5 wt. % of TiO$_2$ (average particle size 0.3 to 0.5 µm) and 2.5 wt. % of polyvinyl alcohol in deionised water with stirring:
220 g of a 5% solution of polyvinyl alcohol in water
95 g of a hydrolysed 22% emulsion of tetramethyl orthosilicate in water
22 g of a 10% solution of the wetting agent Erkantol.

245 ml of deionised water were then added to this mixture and the pH adjusted to 4 with HCl. This dispersion was applied onto a 175 µm gauge PET film to a wet layer thickness of 50 µm and dried at 30° C.

b) Coating the hydrophilic printing plate substrate with a photosensitive monomer layer A Solution was Prepared from the Following Components:
1.6 g of bisimidazole
0.05 g of Michler's ketone
0.1 g of mercaptobenzoxazole
2.1 g of monomer from example 5 26.85 g of 2-butanone; this solution was cast onto the hydrophilic printing plate described in a) as the substrate using a coating knife with a slit width of 30 µm. After drying, the layer thickness was 3.85 µm.

The recording material was brought into contact with a transparent test original with a line pattern of 150 lines per inch and exposed through the test original with UV light.

The exposed recording material was treated with a mixture of 25 wt.% of water and 75 wt.% of ethanol to develop it. Using the printing plate obtained in this manner, it was possible to print on a conventional offset printing press with customary ink. High quality prints (elevated resolution, precise dot reproduction, good acutance) were obtained.

Example 8
Production of an Offset Printing Plate using the Dry Method
a) Production of the photosensitive donor element A solution was prepared from the following components:
1.6 g of bisimidazo 0.05 g of Michler's ketone
0.1 g of mercaptobenzoxazole
2.1 g of monomer from example 5
26.85 g of 2-butanone; this solution was cast onto a 100 μm gauge PET as the substrate using a coating knife with a slit width of 30 μm. After drying, the layer thickness was 3.85 μm.

b) Hydrophilic printing plate substrate from 7a)

The donor element was brought into contact with a transparent test original with a line pattern of 150 lines per inch and exposed through the test original with UV light.

The exposed donor element was then placed in contact on its coated side with the hydrophilic printing plate substrate at 165° C. and passed at a speed of 1.0 m/min through a roller lamination device. The two elements were then separated. The hydrophilic substrate, which was now coated with the photosensitive monomer in a distribution corresponding to the image, was uniformly exposed with UV light. Using the printing plate obtained in this manner, it was possible to print on a conventional offset printing press with customary ink. High quality prints (elevated resolution, precise dot reproduction, good acutance) were obtained.

We claim:

1. Monomers of the formula I

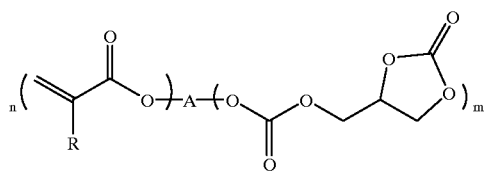

in which

A means an (n+m)-valent unsubstituted or OH subsubstituted hydrocarbon residue with 3 to 30 C atoms, and optionally contains up to 8 ether bridges, R means H or methyl;

n means an integer from 1 to 5;

m means an integer from 1 to 3, providing that n+m is at least 3.

2. The monomers as claimed in claim 1, wherein A is selected from the group consisting of:

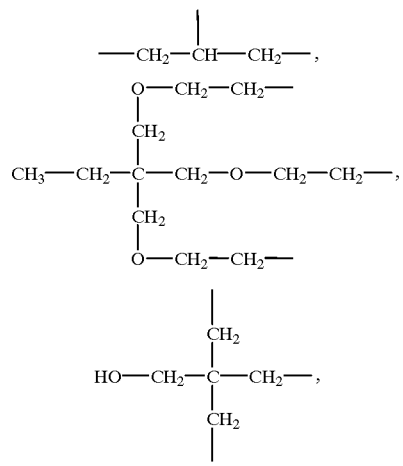

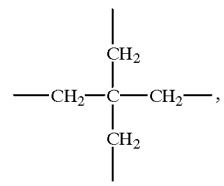

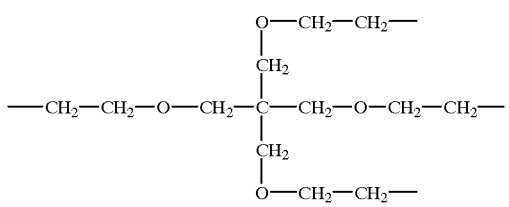

and

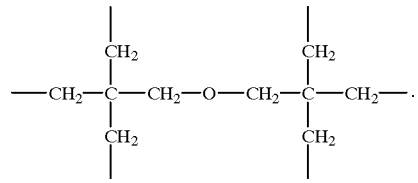

3. Photosensitive recording material comprising at least one photosensitive layer arranged on a support, which layer contains monomers of the formula I

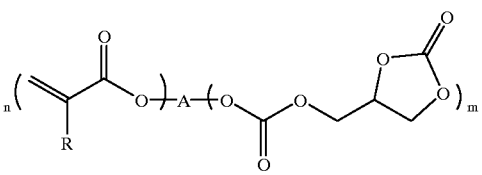

in which

A means an (n+m)-valent unsubstituted or substituted hydrocarbon residue with 3 to 30 C atoms, which may be OH-substituted and may contain up to 8 ether bridges, R means H or methyl;

n means an integer from 1 to 5;

m means an integer from 1 to 3, providing that n+m is at least 3 and at least one photoinitiator.

4. The photosensitive recording material as claimed in claim 3, wherein A is selected from the group consisting of:

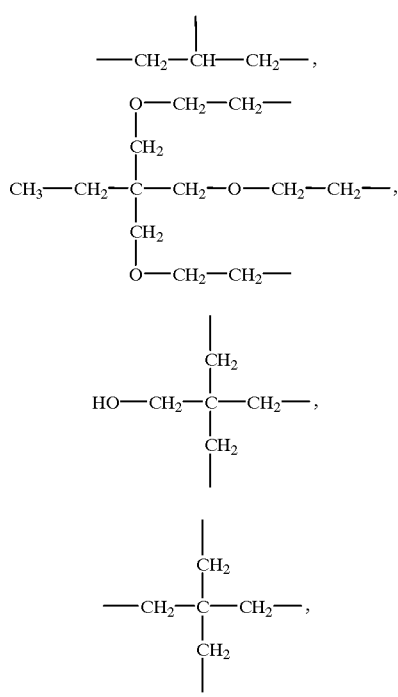

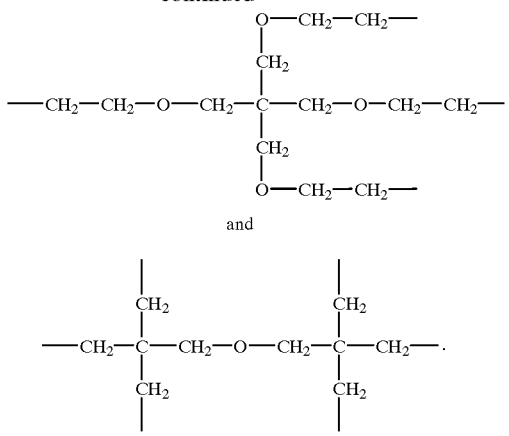

and

—CH₂—C(CH₂)(CH₂)—CH₂—O—CH₂—C(CH₂)(CH₂)—CH₂—.

5. A production of a printing plate comprising the step of producing a polymer image on the recording material as claimed in claim 3 by imagewise exposure of said recording material to actinic radiation and subsequent dry or wet development processing,
wherein the polymer image is produced either directly on the printing plate substrate or
is produced on a donor element and is subsequently transferred to the printing plate substrate.

* * * * *